US012672975B2

(12) United States Patent
Jih

(10) Patent No.: US 12,672,975 B2
(45) Date of Patent: Jul. 7, 2026

(54) KNEE PAD BRACKET

(71) Applicant: Yong-Pei Jih, Chiayi County (TW)

(72) Inventor: Yong-Pei Jih, Chiayi County (TW)

( * ) Notice: Subject to any disclaimer, the term of this patent is extended or adjusted under 35 U.S.C. 154(b) by 691 days.

(21) Appl. No.: 18/121,110

(22) Filed: Mar. 14, 2023

(65) Prior Publication Data

US 2023/0372135 A1 Nov. 23, 2023

(30) Foreign Application Priority Data

May 20, 2022 (TW) .................................. 111118871

(51) Int. Cl.
*A61F 5/01* (2006.01)
*A61H 23/02* (2006.01)

(52) U.S. Cl.
CPC .......... *A61F 5/0123* (2013.01); *A61H 23/02* (2013.01); *A61F 2005/0197* (2013.01); *A61H 2201/0107* (2013.01); *A61H 2201/0184* (2013.01); *A61H 2201/1642* (2013.01); *A61H 2201/1652* (2013.01); *A61H 2201/5064* (2013.01); *A61H 2201/5069* (2013.01); *A61H 2205/102* (2013.01)

(58) Field of Classification Search
CPC ............ A41D 13/065; A41D 2400/322; A61F 2005/0197; A61F 5/0118; A61F 5/013; A61H 2205/102; A61H 23/02
See application file for complete search history.

(56) References Cited

U.S. PATENT DOCUMENTS

| 8,939,924 B1 * | 1/2015 | Paulos ...................... A61F 5/01 |
| | | 602/5 |
| 9,622,900 B2 | 4/2017 | Knecht |
| 2008/0200856 A1 * | 8/2008 | Cadichon .............. A61F 5/0123 |
| | | 602/26 |
| 2019/0069614 A1 * | 3/2019 | Feltner ................. A41D 13/065 |
| 2020/0121485 A1 * | 4/2020 | Mcdaid .................. A61H 1/024 |

FOREIGN PATENT DOCUMENTS

| CA | 3084026 A1 * | 6/2019 | ........... A61F 5/0123 |
| CN | 204121220 U | 1/2015 | |
| CN | 204766077 U * | 11/2015 | |
| CN | 107714259 A * | 2/2018 | ........... A61B 5/1116 |
| CN | 111629699 A | 9/2020 | |

(Continued)

*Primary Examiner* — Kendra D Carter
*Assistant Examiner* — Akhil Adai Jayan
(74) *Attorney, Agent, or Firm* — Troutman Pepper Locke LLP; Tim Tingkang Xia, Esq.

(57) ABSTRACT

The present invention is a knee pad bracket, which comprises: a first frame, having a first arc portion and two first support rods; a second frame, having a second arc portion and two second support rods, the first arc portion defines a first accommodation room; a third frame, having a third arc portion and two third support rods; a fourth frame, having a fourth arc portion and two fourth support rods to define a second accommodation room; two pivot axes, pivotally disposed at two corresponding sides of the first, second, third, and fourth frame and pivotally connected with the first, second, third, and fourth support rod; a first elastic element, which two ends being disposed on a same side of the first and second frame; and a second elastic element, which two ends being disposed on a same side of the third and fourth frame.

13 Claims, 4 Drawing Sheets

(56)          References Cited

FOREIGN PATENT DOCUMENTS

| | | | | | |
|---|---|---|---|---|---|
| CN | 113491607 | A | | 10/2021 | |
| CN | 114392019 | A | | 4/2022 | |
| KR | 20210157247 | A | * | 12/2021 | ........... A61F 5/0585 |
| TW | M458211 | U | | 8/2013 | |
| WO | 2019122364 | A1 | | 6/2019 | |
| WO | WO-2021032970 | A1 | * | 2/2021 | ........... A63F 13/212 |

* cited by examiner

KNEE PAD BRACKET

CROSS-REFERENCE TO RELATED APPLICATIONS

This non-provisional application claims priority under 35 U.S.C. § 119(a) on Patent Application Nos). 111118871 filed in Taiwan on May 20, 2022, the entire contents of which are hereby incorporated by reference.

BACKGROUND OF THE INVENTION

1. Field of the Invention

The present invention generally relates to a medical auxiliary tool, more particularly to a knee pad bracket.

2. Description of the Prior Art

The knee pad bracket is to protect knees or keep correct postures while walking. The most common knee pad bracket is a sleeve type, which is a one-piece design, in order to wrap around the knee. The shortcoming is that the area of wrapping around the knee is very large, so that the user may have hot feeling while wrapping for a long time. The other knee pad bracket is able to adjust the tightness depending on the body sizes of different users. Generally speaking, Velcro is the way to adjust the tightness, but sometimes the flexibility of Velcro is worse, and it causes that the effect of shock absorption cannot be approached. The third type of the knee pad bracket is a mechanical bone type, which has the feature of strong resistance fixation. Due to complicate processes in use and installment, easy slip and high price, it is not welcome in the market. Besides, the prior knee pad brackets only function to approach fixation, and it is not possible to relieve the sore feeling from a knee. As a conclusion, a new knee pad bracket product with comfortable wear and absorbing forces from different directions applied onto the knee in order to ease the pressures on the knee, persistent fixation and massaging the knee will be a trend in the market.

SUMMARY OF THE INVENTION

The present invention provides a knee pad bracket, which functions are that of shock absorption and massage, so as to protect the knee(s) of a wearer.

The knee pad bracket comprises: a first frame, having a first arc portion and two first support rods that are disposed at two ends of the first arc portion respectively; a second frame, having a second arc portion and two second support rods that are disposed at two ends of the second arc portion individually, wherein the first arc portion corresponds to the second arc portion, in order to define a first accommodation room that accommodates a thigh of a human being; a third frame, which corresponds to the first frame, having a third arc portion and two third support rods that are disposed at two ends of the third arc portion respectively; a fourth frame, which corresponds to the second frame, having a fourth arc portion and two fourth support rods that are disposed at two ends of the fourth arc portion individually, in order to define a second accommodation room that is connected with the first accommodation room and accommodates a calf of the human being; two pivot axes, detachably and pivotally disposed at two corresponding sides of the first frame, the second frame, the third frame, and the fourth frame and pivotally connected with the first support rod, the second support rod, the third support rod, and the fourth support rod;

a first elastic element, which two ends being disposed on a same side of the first frame and the second frame, wherein the same side is opposite to another same side, corresponding to the first accommodation room, of the first frame and the second frame; and a second elastic element, which two ends being disposed on a same side of the third frame and the fourth frame, wherein the same side is opposite to another same side, corresponding to the second accommodation room, of the third frame and the fourth frame.

Preferably, the first frame is formed by stacking a plurality of first subframes and the two first subframes next to each other are able to move correspondingly; the second frame being formed by stacking a plurality of second subframes and the two second subframes next to each other being able to move correspondingly; the third frame being formed by stacking a plurality of third subframes and the two third subframes next to each other being able to move correspondingly; and the fourth frame being formed by stacking a plurality of fourth subframes and the two fourth subframes next to each other being able to move correspondingly.

Preferably, the knee pad bracket further comprises a cushion, which is disposed at a side between the first frame and the first accommodation room, a side between the second frame and the first accommodation room, a side between the third frame and the second accommodation room, or a side between the fourth frame and the second accommodation room.

Preferably, a material for the first frame, the second frame, the third frame, and the fourth frame is selected from the group consisting of: plastic, silicone, carbon fiber, and ultra-thin tough metal sheet.

Preferably, an angle $\Theta 1$ is between a central axis of the first arc portion and a central axis of the first support rod and faces to the third frame, the angle $\Theta 1$ being less or equal to $135°$ and greater or equal to $100°$; an angle $\Theta 2$ is between a central axis of the second arc portion and a central axis of the second support rod and faces to the fourth frame, the angle $\Theta 2$ being less or equal to $135°$ and greater or equal to $100°$; an angle $\Theta 3$ is between a central axis of the third arc portion and a central axis of the third support rod and faces to the first frame, the angle $\Theta 3$ being less or equal to $135°$ and greater or equal to $100°$; and an angle $\Theta 4$ is between a central axis of the fourth arc portion and a central axis of the fourth support rod and faces to the second frame, being less or equal to $135°$ and greater or equal to $100°$.

Preferably, the angles $\Theta 1$, $\Theta 2$, $\Theta 3$, and $\Theta 4$ are equal to each other.

Preferably, the present invention further comprises a vibration module, which is disposed at a side opposite to another side of the first frame facing to the first accommodation room; a side opposite to another side of the second frame facing to the first accommodation room; a side opposite to another side of the third frame facing to the second accommodation room; or a side opposite to another side of the fourth frame facing to the second accommodation room.

Preferably, the present invention further comprises a control module, which is electrically connected with the vibration module and a touch device, the control module having: a data output unit, transforming vibration frequencies, vibration rates and vibration directions from the vibration module into vibration information and outputting the vibration information to the touch device; and a data input unit, the touch device modulating the vibration information for transmitting the modulated vibration information to the data input unit, in order to control the vibration frequencies, the vibration rates and the vibration directions from the vibration module by means of the control module.

Preferably, the present invention further comprises a an inclining sensing module, electrically connected with the control module and sensing a tilt angle of the knee pad bracket, the tilt angle being transformed into and stored in a form of tilt information, continuously the tilt information being transmitted to the data input unit; and an alarm module, electrically connected with the control module, the control module communicating with the alarm module to generate an alarm signal, which is transmitted to the touch device via the data output unit while the tilt information is producing drastic changes.

Preferably, the present invention further comprises a distance detection module, electrically connected with the control module and detecting a distance between the knee pad bracket and an environment, the distance being transformed into and stored in a form of distance information, continuously the distance information being transmitted to the data input unit; and an alarm module, electrically connected with the control module, the control module communicating with the alarm module to generate an alarm signal, which is transmitted to the touch device via the data output unit while the distance information is less than 30 cm.

Preferably, the present invention further comprises a positioning module, which is electrically connected with the control module, and stores a location information according to the geographic location of the kneecap brace, in order to transmit the location information to the touch device via the data output unit.

Compared to prior arts, the knee pad bracket of the present invention can absorb different directions of forces applied to the human legs, in order to relieve the pressure on the knee, avoid sprains caused by excessive range of motion or incorrect movements, or excessive wear of the knee articular cartilage. The vibration module 16 can massage the knee and relieve soreness in the wearer's knees by means of wearing devices, mobile phones or tablets controlling the vibration rates, vibration frequencies and vibration directions thereof. The present invention combines the advantages of the sleeve type knee pad bracket and the winding type knee pad bracket, and is highly stable in the aspect of structure. It is able to adjust the tightness of the first elastic element and the second elastic element based on the body shapes of different users. In addition, the knee pad bracket of the present invention is with outstanding air permeability and heat dissipation, and comfortable to wear for a long-term as well. Further, the knee pad bracket is constructed by a multi-layer structure, which is with higher structural strength, bending resistance, and a longer service life.

Other and further features, advantages, and benefits of the invention will become apparent in the following description taken in conjunction with the following drawings. It is to be understood that the foregoing general description and following detailed description are exemplary and explanatory but are not to be restrictive of the invention. The accompanying drawings are incorporated in and constitute a part of this application and, together with the description, serve to explain the principles of the invention in general terms. Like numerals refer to like parts throughout the disclosure.

BRIEF DESCRIPTION OF THE DRAWINGS

The objects, spirits, and advantages of the preferred embodiments of the present invention will be readily understood by the accompanying drawings and detailed descriptions, wherein.

DETAILED DESCRIPTION OF THE INVENTION

Following preferred embodiments and figures will be described in detail so as to achieve aforesaid objects.

Figure 1A:
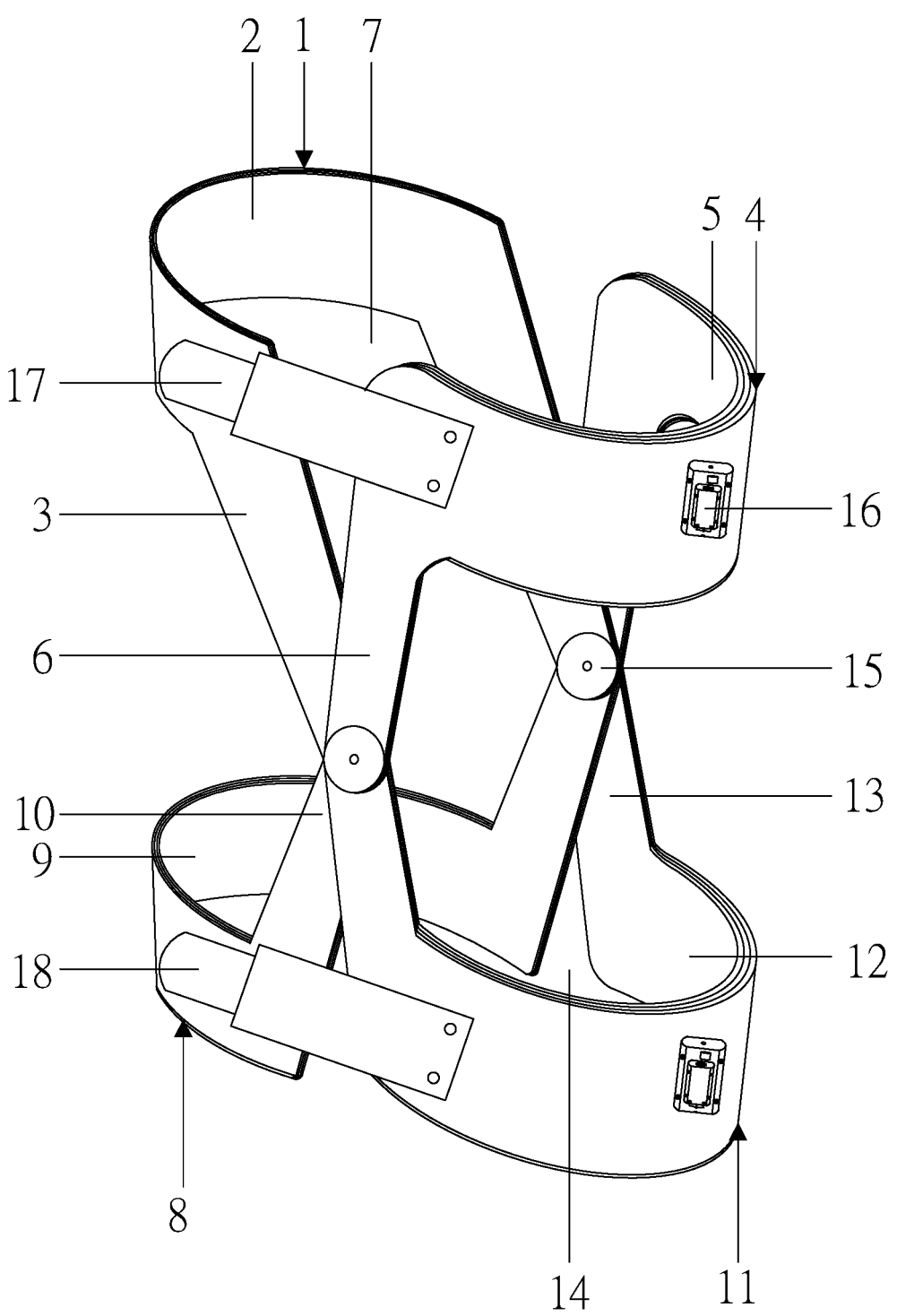
FIG. 1A to FIG. 1C illustrate schematic views of structural characteristics of the present invention.

The present invention provides a knee pad bracket. With reference to FIG. 1A, the knee pad bracket includes: a first frame 1, having a first arc portion 2 and two first support rods 3 that are disposed at two ends of the first arc portion 2 respectively; a second frame 4, having a second arc portion 5 and two second support rods 6 that are disposed at two ends of the second arc portion 5 individually, wherein the first arc portion 2 corresponds to the second arc portion 5, in order to define a first accommodation room 7 that accommodates a thigh of a human being; a third frame 8, which corresponds to the first frame 1, having a third arc portion 9 and two third support rods 10 that are disposed at two ends of the third arc portion 9 respectively; a fourth frame 11, which corresponds to the second frame 4, having a fourth arc portion 12 and two fourth support rods 13 that are disposed at two ends of the fourth arc portion 12 individually, in order to define a second accommodation room 14 that is connected with the first accommodation room 7 and accommodates a calf of the human being; and two pivot axis 15, detachably and pivotally disposed at two corresponding sides of the first frame 1, the second frame 4, the third frame 8, and the fourth frame 11 and pivotally connected with the first support rod 3, the second support rod 6, the third support rod 10, and the fourth support rod 13. It is to be understood that the inner sides of the first arc portion 2 and the second arc portion 5 facing to the first accommodation room 7 touch the outer rim of a thigh to position the first frame 1 and the second frame 4, and the inner sides of the third arc portion 9 and the fourth arc portion 12 facing to the second accommodation room 14 touch the outer rim of a calf to position the third frame 8 and the fourth frame 11. For a preferred embodiment, a material for the first frame 1, the second frame 4, the third frame 8, and the fourth frame 11 is selected from the group consisting of: plastic, silicone, carbon fiber, and ultra-thin tough metal sheet, but not limited thereto.

For enhancing the combination strength of the frames and the pivot axes 15 in order to avoid the conditions of damaging or break while the frames are rotating relative to the pivot axes 15, the material of the pivot axis 15 is metal, but not limited thereto. In a preferred embodiment, the pivot axis 15 has a rotation axis, and the rotating shaft is installed with screws, but not limited thereto. In another preferred embodiment, the purpose to design the pivot axis 15 is to let the frame make rotations corresponding to the pivot axis 15. It is convenient that the frame can be adjusted for the positions itself according to the actions of the human leg while the leg is in motion or bending. So that the leg can achieve the functions of shock absorption, posture adjustment, and sprain prevention in various postures or movements. In another preferred embodiment, the knee brace of the present invention can stabilize the joints of the limbs of the human body to reduce violent vibration and twisting around the joints of the limbs, and promote the stability and the safety while the human body is in motion as well. The structures of the frames are all flexible, in order to share the forces, horizontal or vertical forces, that the human knees receive, and the deformation of the frames are generating. In addition, the frames are able to recover to their original shapes while there are no outer forces applying to the frames.

For massaging the knees, it is to relieve knee pain or relieve knee pressure, please refer to FIG. 1A. As shown in figure, it includes: a vibration module 16, which is disposed at a side opposite to another side of the first frame 1 facing to the first accommodation room 7; a side opposite to another side of the second frame 4 facing to the first accommodation room 7; a side opposite to another side of the third frame 8 facing to the second accommodation room 14; or a side opposite to another side of the fourth frame 11 facing to the second accommodation room 14. It is understandable that the vibration module 16 is not directly in touch with the first accommodation room 7 or the second accommodation room 14 for avoiding the direct contact of the human leg and the vibration module 16. That means the direct contact may cause knee vibrations that are too intense and counterproductive to their relief. In another aspect, sweat contacting with the vibration module 16 directly is avoided as well. In practice, the sweat permeates through the vibration module 16 to cause the damage of the vibration module 16 if the direct contact does happen. Therefore, the life time of the knee pad bracket is highly decreased. For another preferred embodiment, installing more vibration modules 16 on the first frame 1, the second frame 4, the third frame 8, or the fourth frame 11 in order to averagely massage the portion around the knee or enhance the massage force. The numbers for the vibration modules 16 on the first frame 1, the second frame 4, the third frame 8, and the fourth frame 11 may be the same or different. Talking to a better design, the knee pad brackets are able to averagely massage the knee if the numbers for the vibration modules on each of the first frame 1, the second frame 4, the third frame 8, and the fourth frame 11 are the same. In addition, the vibration module 16 is a motor, but not limited thereto.

To absorb the pressure that the knee pad bracket applies to the knee, the present invention plays the functions of reducing the vibrations and lessening the load to the knee. Please refer to FIG. 1A, the present invention further includes a first elastic element 17, which two ends being disposed on a same side of the first frame 1 and the second frame 4, wherein the same side is opposite to another same side, corresponding to the first accommodation room 7, of the first frame 1 and the second frame 4; and a second elastic element 18, which two ends being disposed on a same side of the third frame 8 and the fourth frame 11, wherein the same side is opposite to another same side, corresponding to the second accommodation room 14, of the third frame 8 and the fourth frame 11. For a preferred embodiment, the one end of the first elastic element 17 is firmly disposed at the first frame 1, and the other end of the first elastic element 17 is movably arranged on the second frame 4. The first elastic element 17 is able to move relative to the second frame 4, so that the first frame 1 pivots relative to the pivot axis 15, and it results in that the first frame 1 is close to or away from the second frame 4. On the other hand, the one end of the first elastic element 17 is firmly disposed at the second frame 4, and the other end of the first elastic element 17 is movably arranged on the first frame 1. The first elastic element 17 is able to move relative to the first frame 1, so that the second frame 4 pivots relative to the pivot axis 15, and it results in that the second frame 4 is close to or away from the first frame 1. In another preferred embodiment, the one end of the first elastic element 17 is movably disposed at the first frame 1, and the other end of the first elastic element 17 is movably arranged on the second frame 4. The first elastic element 17 is able to move relative to the second frame 4, so that the first frame 1 pivots relative to the pivot axis 15, and it results in that the first frame 1 is close to or away from the second frame 4. The first elastic element 17 can move relative to the first frame 1, so that the second frame 4 pivots relative to the pivot axis 15, in order to let the second frame 4 be close to or away from the first frame 1. For one more preferred embodiment, to enhance the stability between the first frame 1 and the second frame 4 further has a third elastic element, which two ends are disposed at a side, corresponding to a side that the first frame 1 and the second frame 4 face to the first accommodation room 7, that is, a same outer side of the first frame 1 and the second frame 4. The same outer side corresponds another same outer side, the first elastic element 17 is on, of the first frame 1 and the second frame 4. In practice, the connections among the third elastic element, the first frame 1 and the second frame 4 and the connections among the first elastic element 17, the first frame 1 and the second frame 4 are the same, and they will not be described any further hereinafter.

The one end of the second elastic element 18 is firmly disposed at the third frame 8, and the other end of the second elastic element 18 is movably arranged at the fourth frame 11, as shown in FIG. 1A. The second elastic element 18 moves relative to the fourth frame 11, and thus the third frame 8 pivots relative to the pivot axis 15, in order to let the third frame 8 be close to or away from the fourth frame 11. On the other hand, the one end of the second elastic element 18 is firmly disposed at the fourth frame 11, and the other end of the second elastic element 18 is movably arranged at the third frame 8. The second elastic element 18 moves relative to the third frame 8, and thus the fourth frame 11 pivots relative to the pivot axis 15, in order to let the fourth frame 11 be close to or away from the third frame 8. In a preferred embodiment, the one end of the second elastic element 18 is movably disposed at the third frame 8, and the other end of the second elastic element 18 is movably arranged at the fourth frame 11. The second elastic element 18 moves relative to the fourth frame 11, and thus the third frame 8 pivots relative to the pivot axis 15, in order to let the third frame 8 be close to or away from the fourth frame 11. Also, the second elastic element 18 moves relative to the third frame 8, so as to make the fourth frame 11 relative to the pivot axis 15 for the fourth frame 11 being close to or away from the third frame 8. For one more preferred embodiment, to enhance the stability between the third frame 8 and the fourth frame 11 further has a fourth elastic element, which two ends are disposed at a side, corresponding to a side that the third frame 8 and the fourth frame 11 face to the second accommodation room 14, that is, a same outer side of the third frame 8 and the fourth frame 11. The same outer side corresponds another same outer side, the first elastic element 17 is on, of the third frame 8 and the fourth frame 11. In practice, the connections among the fourth elastic element, the third frame 8 and the fourth frame 11 and the connections among the second elastic element 18, the third frame 8 and the fourth frame 11 are the same, and they will not be described any further hereinafter.

The first elastic element 17, the second elastic element 18, the third elastic element, or the fourth elastic element is a sports bandage, but with no limitation. In a preferred embodiment, the first elastic element 17 or the third elastic element functions to make the first frame 1 and the second frame 4 tightly attach to the thigh of a human being, and also apply a certain pressure to the thigh for stabilizing postures and reducing vibrations while walking. The second elastic element 18 or the fourth elastic element functions to make the third frame 8 and the fourth frame 11 tightly attach to the calf of a human being, and also apply a certain pressure to the calf for stabilizing postures and reducing vibrations while walking.

Figure 1B:
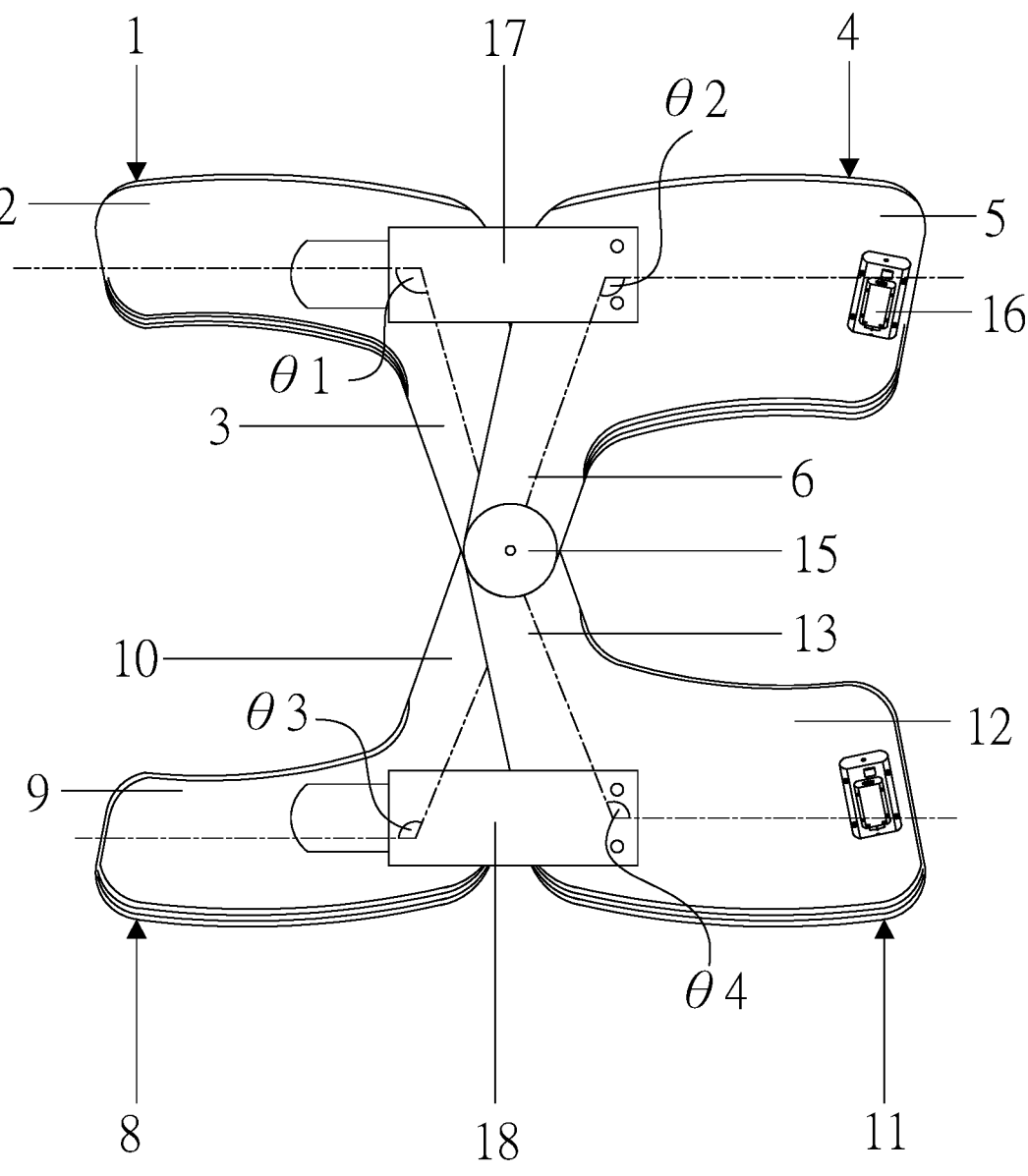

In order to facilitate the pivoting between the frames, the thigh and calf can be closely fitted to the frames, please refer to FIG. 1B. As shown in figure, an angle $\Theta 1$ is between a central axis of the first arc portion 2 and a central axis of the first support rod 3 and faces to the third frame 8, the angle $\Theta 1$ being less or equal to 135° and greater or equal to 100°; an angle $\Theta 2$ is between a central axis of the second arc portion 5 and a central axis of the second support rod 6 and faces to the fourth frame 11, the angle $\Theta 2$ being less or equal to 135° and greater or equal to 100°; an angle $\Theta 3$ is between a central axis of the third arc portion 9 and a central axis of the third support rod 10 and faces to the first frame 1, the angle $\Theta 3$ being less or equal to 135° and greater or equal to 100°; and an angle $\Theta 4$ is between a central axis of the fourth arc portion 12 and a central axis of the fourth support rod 13 and faces to the second frame 4, being less or equal to 135° and greater or equal to 100°. In a preferred embodiment, the angles $\Theta 1$, $\Theta 2$, $\Theta 3$, and $\Theta 4$ are equal to each other, but without any limitations.

Figure 1C:
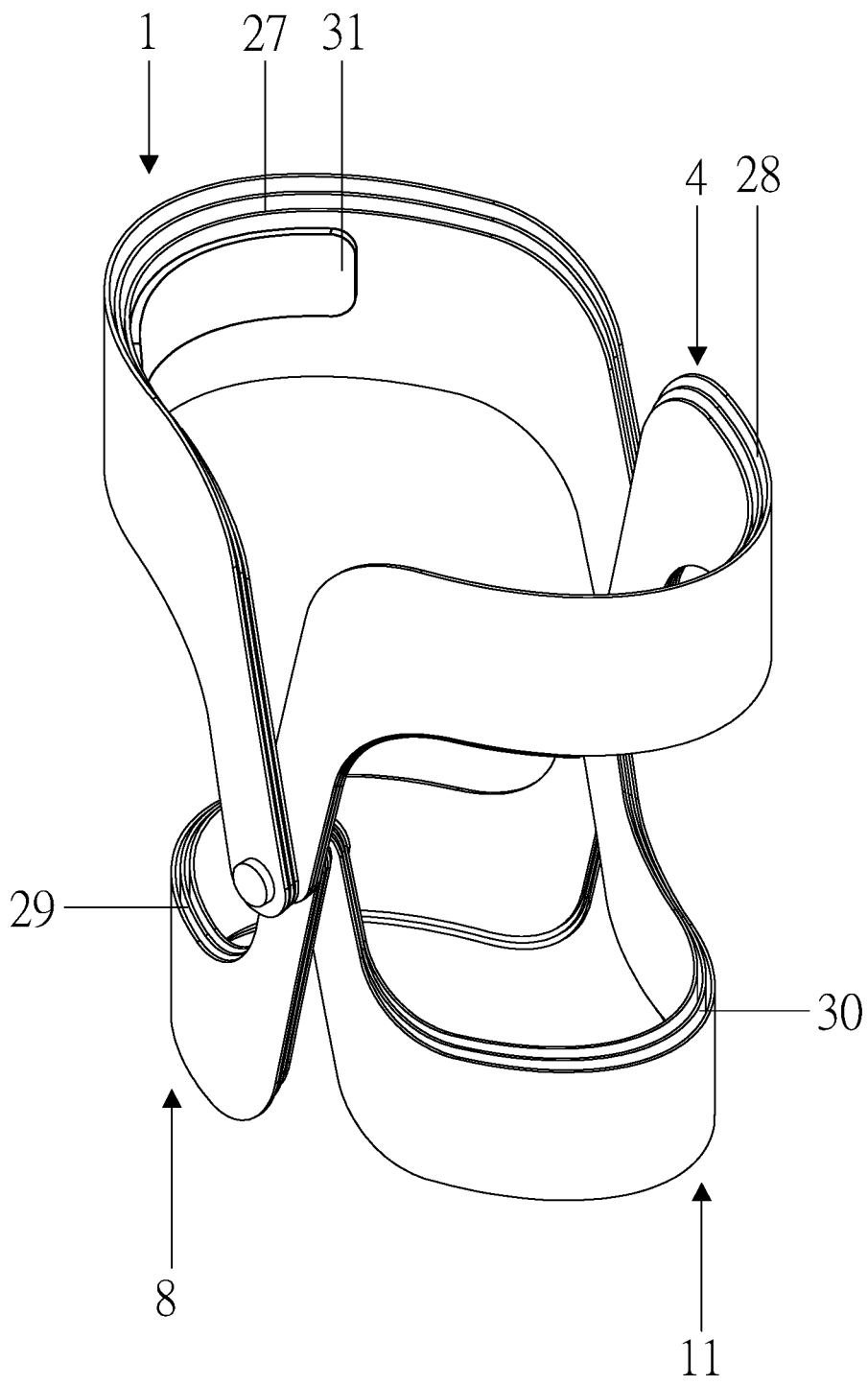

According to FIG. 1C, the first frame 1 is formed by stacking a plurality of first subframes 27 and the two first subframes 27 next to each other are able to move correspondingly; the second frame 4 being formed by stacking a plurality of second subframes 28 and the two second subframes 28 next to each other being able to move correspondingly; the third frame 8 being formed by stacking a plurality of third subframes 29 and the two third subframes 29 next to each other being able to move correspondingly; and the fourth frame 11 being formed by stacking a plurality of fourth subframes 30 and the two fourth subframes 30 next to each other being able to move correspondingly. In practice, both the first subframes 27, the second subframes 28, the third subframes 29, and the fourth subframes 30 are not adhered to each other. Therefore, between the first subframes 27, the second subframes 28, the third subframes 29, and the fourth subframes 30 generate a friction force while the knee is bending or vibrating. This frictional force can offset the force exerted by the human knee on each frame, so the force on the knee can be reduced to reduce the load on the knee. For example, the knee support bracket of the present invention can offset the forces in all directions on the human leg, in order to relieve the pressure on the knee, and avoid sprains caused by excessive movement or incorrect movements, or excessive wear of the knee articular cartilage, while the human body is running, jumping, squatting, or swinging. In a preferred embodiment, the number of the first subframe 27, the second subframe 28, the third subframe 29, and the fourth subframe 30 is more, the friction force is larger, and the effect of reducing vibrations is better. On the other hand, to avoid an excessive friction force to make the leg hardly move, an A is less than 7 but greater than 1 and defined as the number of the first subframe 27, a B is less than 7 but greater than 1 and defined as the number of the second subframe 28, a C is less than 7 but greater than 1 and defined as the number of the third subframe 29, and a D is less than 7 but greater than 1 and defined as the number of the fourth subframe 30. For another preferred embodiment, if the vibration module 16 is activated, not only the knee is massaged, but also the effect of reducing vibrations to the knee pad bracket is promoted. For another preferred embodiment, the vibration module 16 is a motor, but not limited thereto. In another preferred embodiment, a material for the first subframe 27, the second subframe 28, the third subframe 29, and the fourth subframe 30 is selected from the group consisting of: plastic, silicone, carbon fiber, and ultra-thin tough metal sheet, but without any limitation. Specifically, when each frame receives a load impact, it becomes a stretching motion, which will cause strong friction between the two sub-frames (extrusion and stretching phenomenon), simultaneously the two friction surfaces will produce motion friction in two different directions to achieve the purpose of shock absorption. For further preferred embodiment, to enhance the comfort of the thigh or calf wearing the knee pad bracket, in order to reduce sense of oppression that the knee pad bracket to the thigh or calf, the present invention further has: a cushion 31, which is disposed at a side between the first frame 1 and the first accommodation room 7, a side between the second frame 4 and the first accommodation room 7, a side between the third frame 8 and the second accommodation room 14, or a side between the fourth frame 4 and the second accommodation room 14. For more preferred embodiments, the cushion 31 is made by gel, silicone, or rubber, but not limited thereto.

For controlling the vibration rate, vibration frequency, and vibration direction of the vibration module 16, the user massage the knees depending on the preferences or needs. Therefore, please refer to FIG. 2. The present invention further has a control module 19, which is electrically connected with the vibration module 16 and a touch device 20, wherein the control module 19 has a data output unit (21), transforming vibration frequencies, vibration rates and vibration directions from the vibration module 16 into vibration information and outputting the vibration information to the touch device 20; and a data input unit 22, wherein the touch device 20 modulates the vibration information for transmitting the modulated vibration information to the data input unit 22, in order to control the vibration frequencies, the vibration rates and the vibration directions from the vibration module 16 by means of the control module 19. In a preferred embodiment, the touch device is one of the following group consisting of: smart watch, smart bracelet, mobile phone, laptop, or tablet, but not limited thereto.

Figure 2:
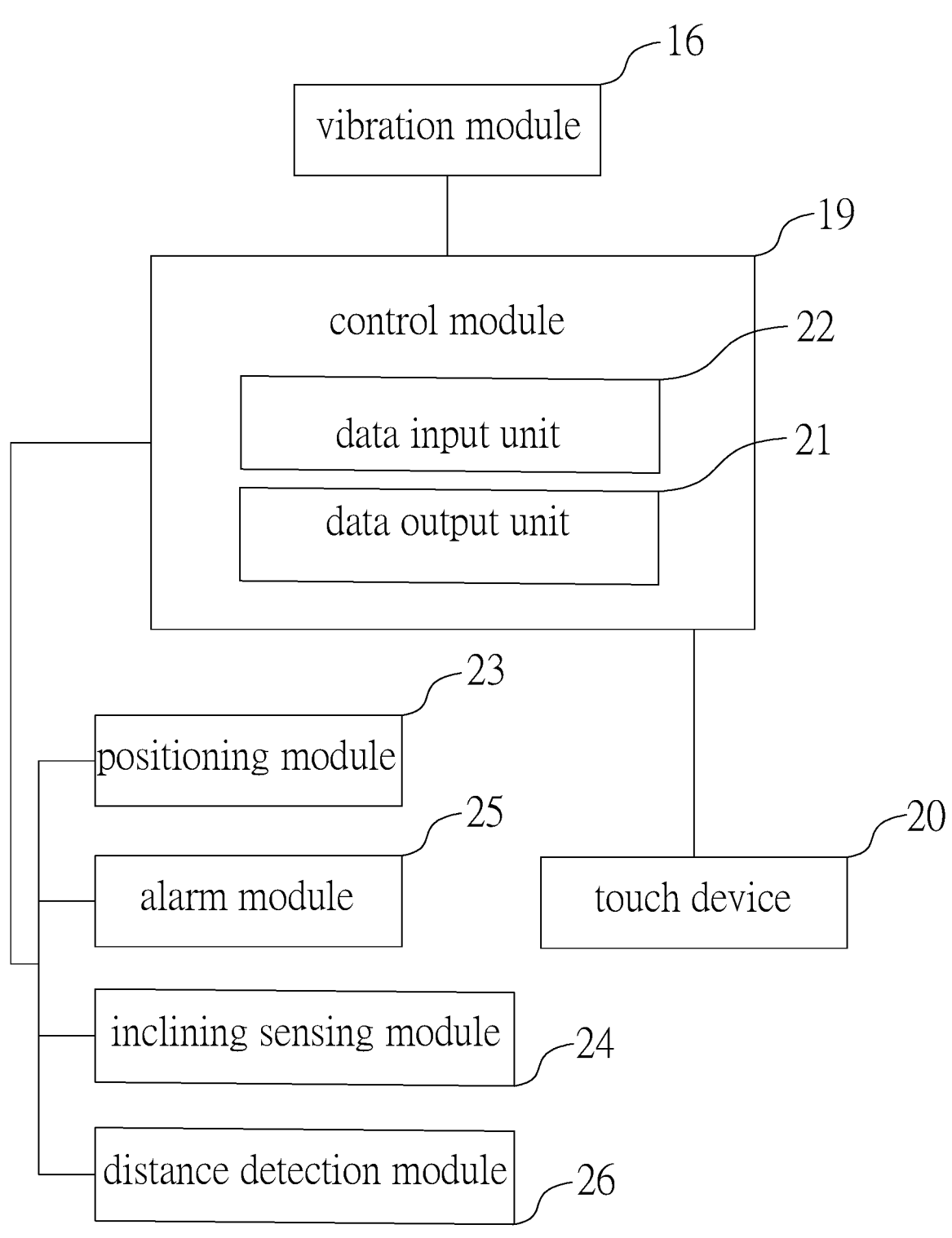
FIG. 2 illustrates a block diagrams of connection relationships among modules of the present invention.

To ensure whether the user is in a fallen state, or to warn passers-by around the patient, relatives and friends of the patient, or medical staff, please refer to FIG. 2. The present invention further has an inclining sensing module 24, which is electrically connected with the control module 19 and senses a tilt angle of the knee pad bracket, the tilt angle is transformed into and stored in a form of tilt information, continuously the tilt information is transmitted to the data input unit 22; and an alarm module 25, which is electrically connected with the control module 19, and the control module 19 communicates with the alarm module 25 to generate an alarm signal, which is transmitted to the touch device 20 via the data output unit 21 while the tilt information is producing drastic changes. In another preferred embodiment, to confirm the position information of the user wearing the knee pad bracket, the present invention further has a positioning module 23, which is electrically connected with the control module 19, and stores a location information according to the geographic location of the kneecap brace, in order to transmit the location information to the touch device 20 via the data output unit 21. Specifically, the touch device 20 is remotely controlled by the user wearing the knee pad bracket, relatives, friends, or medical staff. When the injury of the user's knee is relatively slight, or it is only used to adjust the walking posture, the user is capable of controlling the touch device 20 by himself. On the other hand, when the user's knee injury is relatively serious, or the user is an elder whose self-protection ability is poor, therefore, the user's relatives, friends, or medical staff can use the touch device 20 to monitor the user's physical state. When the position of the user is far from the range of daily activities, the user falls down because of an unbalanced center of gravity, or touches a barricade to fall down, so as to cause the knee pad bracket to tilt sharply, the control module 19 transmits the alarm signal to the touch device 20, thus the user's relatives, friends, or medical staff are able to process the emergency situation for remotely taking care of the user.

To avoid the user falling down by a barricade, or accidentally touches a barricade, please refer to FIG. 2. The present invention further has a distance detection module 26, which is electrically connected with the control module 19 and detects a distance between the knee pad bracket and an environment, and the distance is transformed into and stored in a form of distance information, continuously the distance information is transmitted to the data input unit 22; and an alarm module 25, which is electrically connected with the control module 19, and the control module 19 communicates with the alarm module 25 to generate the alarm signal, which is transmitted to the touch device 20 via the data output unit 21 while the distance information is less than 30 cm.

Compared to prior arts, the knee pad bracket of the present invention can absorb different directions of forces applied to the human legs, in order to relieve the pressure on the knee, avoid sprains caused by excessive range of motion or incorrect movements, or excessive wear of the knee articular cartilage. The vibration module 16 can massage the knee and relieve soreness in the wearer's knees by means of wearing devices, mobile phones or tablets controlling the vibration rates, vibration frequencies and vibration directions thereof. The present invention combines the advantages of the sleeve type knee pad bracket and the winding type knee pad bracket, and is highly stable in the aspect of structure. It is able to adjust the tightness of the first elastic element and the second elastic element based on the body shapes of different users. In addition, the knee pad bracket of the present invention is with outstanding air permeability and heat dissipation, and comfortable to wear for a long-term as well. Further, the knee pad bracket is constructed by a multi-layer structure, which is with higher structural strength, bending resistance, and a longer service life.

Although the invention has been disclosed and illustrated with reference to particular embodiments, the principles involved are susceptible for use in numerous other embodiments that will be apparent to persons skilled in the art. This invention is, therefore, to be limited only as indicated by the scope of the appended claims.

What is claimed is:

1. A knee pad bracket, comprising:
   a first frame (1), having a first arc portion (2) and two first support rods (3) that are disposed at two ends of the first arc portion (2) respectively;
   a second frame (4), having a second arc portion (5) and two second support rods (6) that are disposed at two ends of the second arc portion (5) individually, wherein the first arc portion (2) corresponds to the second arc portion (5), in order to define a first accommodation room (7) that accommodates a thigh of a human being;
   a third frame (8), which corresponds to the first frame (1), having a third arc portion (9) and two third support rods (10) that are disposed at two ends of the third arc portion (9) respectively;
   a fourth frame (11), which corresponds to the second frame (4), having a fourth arc portion (12) and two fourth support rods (13) that are disposed at two ends of the fourth arc portion (12) individually, in order to define a second accommodation room (14) that is connected with the first accommodation room (7) and accommodates a calf of the human being;
   two pivot axes (15), detachably and pivotally disposed at two corresponding sides of the first frame (1), the second frame (4), the third frame (8), and the fourth frame (11), wherein each of the two pivot axes (15) is pivotally connected with one of the first support rods (3), one of the second support rods (6), one of the third support rods (10), and one of the fourth support rods (13);
   a first elastic element (17), which two ends being disposed on a first side of the first frame (1) and a first side of the second frame (4), wherein the first side of the first frame (1) and the first side of the second frame (4) are on the same side, and wherein the first side of the first frame (1) is opposite to a second side of the first frame (1) corresponding to the first accommodation room (7), and the first side of the second frame (4) is opposite to a second side of the second frame (4) corresponding to the first accommodation room (7); and
   a second elastic element (18), which two ends being disposed on a first side of the third frame (8) and a first side of the fourth frame (11), wherein the first side of the third frame (8) and the first side of the fourth frame (11) are on the same side, and wherein the first side of the third frame (8) is opposite to a second side of the third frame (8) corresponding to the second accommodation room (14), and the first side of the fourth frame (11) is opposite to a second side of the fourth frame (11) corresponding to the second accommodation room (14), wherein an angle $\Theta 1$ is between a central axis of the first arc portion (2) and a central axis of the first support rod (3) and faces to the third frame (8), the angle $\Theta 1$ being between 100 degrees and 135 degrees; an angle $\Theta 2$ is between a central axis of the second arc portion (5) and a central axis of the second support rod (6) and faces to the fourth frame (11), the angle $\Theta 2$ being between 100 degrees and 135 degrees; an angle $\Theta 3$ is between a central axis of the third arc portion (9) and a central axis of the third support rod (10) and faces to the first frame (1), the angle $\Theta 3$ being between 100 degrees and 135 degrees; and an angle $\Theta 4$ is between a central axis of the fourth arc portion (12) and a central axis of the fourth support rod (13) and faces to the second frame (4), the angle $\Theta 4$ being between 100 degrees and 135 degrees.

2. The knee pad bracket according to claim 1, wherein the first frame (1) is formed by stacking two first subframes (27) and the two first subframes (27) next to each other are able to move correspondingly; the second frame (4) is formed by stacking two second subframes (28) and the two second subframes (28) next to each other are able to move correspondingly; the third frame (8) is formed by stacking two third subframes (29) and the two third subframes (29) next to each other are able to move correspondingly; and the fourth frame (11) is formed by stacking two fourth subframes (30) and the two fourth subframes (30) next to each other are able to move correspondingly.

3. The knee pad bracket according to claim 2, further comprises a vibration module (16), which is disposed at an outer side of the first frame (1) opposite to an inner side of the first frame (1) facing the first accommodation room (7); an outer side of the second frame (4) opposite to an inner side of the second frame (4) facing the first accommodation room (7); an outer side of the third frame (8) opposite to an inner side of the third frame (8) facing to the second accommodation room (14); or an outer side of the fourth frame (11) opposite to an inner side of the fourth frame (11) facing the second accommodation room (14).

4. The knee pad bracket according to claim 1, further comprises a cushion (31), which is disposed at a side between the first frame (1) and the first accommodation room (7), a side between the second frame (4) and the first accommodation room (7), a side between the third frame (8) and the second accommodation room (14), or a side between the fourth frame (4) and the second accommodation room (14).

5. The knee pad bracket according to claim 4, further comprises a vibration module (16), which is disposed at an outer side of the first frame (1) opposite to an inner side of the first frame (1) facing the first accommodation room (7); an outer side of the second frame (4) opposite to an inner side of the second frame (4) facing the first accommodation room (7); an outer side of the third frame (8) opposite to an inner side of the third frame (8) facing to the second accommodation room (14); or an outer side of the fourth frame (11) opposite to an inner side of the fourth frame (11) facing the second accommodation room (14).

6. The knee pad bracket according to claim 1, wherein a material for the first frame (1), the second frame (4), the third frame (8), and the fourth frame (11) is selected from the group consisting of: plastic, silicone, carbon fiber, and ultra-thin tough metal sheet.

7. The knee pad bracket according to claim 6, further comprises a vibration module (16), which is disposed at an outer side of the first frame (1) opposite to an inner side of the first frame (1) facing the first accommodation room (7); an outer side of the second frame (4) opposite to an inner side of the second frame (4) facing the first accommodation room (7); an outer side of the third frame (8) opposite to an inner side of the third frame (8) facing to the second accommodation room (14); or an outer side of the fourth frame (11) opposite to an inner side of the fourth frame (11) facing the second accommodation room (14).

8. The knee pad bracket according to claim 1, wherein the angles $\Theta 1$, $\Theta 2$, $\Theta 3$, and $\Theta 4$ are equal to each other.

9. The knee pad bracket according to claim 8, further comprises a vibration module (16), which is disposed at an outer side of the first frame (1) opposite to an inner side of the first frame (1) facing the first accommodation room (7); an outer side of the second frame (4) opposite to an inner side of the second frame (4) facing the first accommodation room (7); an outer side of the third frame (8) opposite to an inner side of the third frame (8) facing to the second accommodation room (14); or an outer side of the fourth frame (11) opposite to an inner side of the fourth frame (11) facing the second accommodation room (14).

10. The knee pad bracket according to claim 1, further comprises a vibration module (16), which is disposed at an outer side of the first frame (1) opposite to an inner side of the first frame (1) facing the first accommodation room (7); an outer side of the second frame (4) opposite to an inner side of the second frame (4) facing the first accommodation room (7); an outer side of the third frame (8) opposite to an inner side of the third frame (8) facing to the second accommodation room (14); or an outer side of the fourth frame (11) opposite to an inner side of the fourth frame (11) facing the second accommodation room (14).

11. The knee pad bracket according to claim 10, further comprises a control module (19), which is electrically connected with the vibration module (16) and a touch device (20), the control module (19) having:

a data output unit (21), transforming vibration frequencies, vibration rates and vibration directions from the vibration module (16) into vibration information and outputting the vibration information to the touch device (20); and a data input unit (22), the touch device (20) modulating the vibration information for transmitting the modulated vibration information to the data input unit (22), in order to control the vibration frequencies, the vibration rates and the vibration directions from the vibration module (16) by means of the control module (19).

12. The knee pad bracket according to claim 11, further comprises:

an inclining sensing module (24), electrically connected with the control module (19) and sensing a tilt angle of the knee pad bracket, the tilt angle being transformed into and stored in a form of tilt information, continuously the tilt information being transmitted to the data input unit (22); and an alarm module (25), electrically connected with the control module (19), the control module (19) communicating with the alarm module (25) to generate an alarm signal, which is transmitted to the touch device (20) via the data output unit (21) while the tilt information is producing changes.

13. The knee pad bracket according to claim 11, further comprises a distance detection module (26), electrically connected with the control module (19) and detecting a distance between the knee pad bracket and an environment, the distance being transformed into and stored in a form of distance information, continuously the distance information being transmitted to the data input unit (22); and an alarm module (25), electrically connected with the control module (19), the control module (19) communicating with the alarm module (25) to generate an alarm signal, which is transmitted to the touch device (20) via the data output unit (21) while the distance information is less than 30 cm.

* * * * *